(12) United States Patent  (10) Patent No.: US 6,963,011 B2
Bernstein                  (45) Date of Patent: *Nov. 8, 2005

(54) N-(2-PHENYL-3-AMINOPROPYL) NAPHTHAMIDES

(75) Inventor: Peter Bernstein, Wallingford, PA (US)

(73) Assignee: Astrazeneca AB, Sodertalje (SE)

( * ) Notice: Subject to any disclaimer, the term of this patent is extended or adjusted under 35 U.S.C. 154(b) by 176 days.

This patent is subject to a terminal disclaimer.

(21) Appl. No.: 10/333,658
(22) PCT Filed: Jul. 31, 2001
(86) PCT No.: PCT/SE01/01687
§ 371 (c)(1), (2), (4) Date: Jan. 21, 2003
(87) PCT Pub. No.: WO02/12168
PCT Pub. Date: Feb. 14, 2002

(65) Prior Publication Data
US 2004/0014809 A1 Jan. 22, 2004

(30) Foreign Application Priority Data
Aug. 4, 2000 (GB) .............................. 0019008

(51) Int. Cl.$^7$ .................... C07C 233/65; A61K 31/165
(52) U.S. Cl. ...................................... 564/180; 514/617
(58) Field of Search .......................... 564/180; 514/617

(56) References Cited

U.S. PATENT DOCUMENTS 6,476,077 B1 * 11/2002 Bernstein .................... 514/620

FOREIGN PATENT DOCUMENTS

EP        0432442 A1   6/1991
WO   WO0064423 A2   11/2000

* cited by examiner

Primary Examiner—Shailendra Kumar
(74) Attorney, Agent, or Firm—Astrazeneca Pharmaceuticals; Cozen O'Connor, P.C.

(57) ABSTRACT

A compound of the formula:

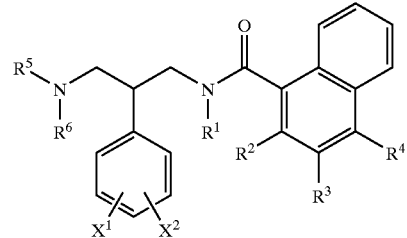

wherein $R^1$, $R^2$, $R^3$, $R^4$, $R^5$, $R^6$, $X^1$ and $X^2$ are as defined in the specification useful for the treatment of diseases in which action of the neurokinin 1 receptor is implicated, methods of using such compounds and pharmaceutical compositions comprising such compounds.

6 Claims, No Drawings

N-(2-PHENYL-3-AMINOPROPYL) NAPHTHAMIDES

This a section 371 filing of International Application PCT/SE01/01687, filed Jul. 31, 2001, which claims section 119 priority to Application No. 0019008.2 filed in the UK on Aug. 4, 2000.

BACKGROUND

The mammalian neurokinins comprise a class of peptide neurotransmitters which are found in the peripheral and central nervous systems. The three principal neurokinins are Substance P(SP), Neurokinin A (NKA) and Neurokinin B (NKB).

There are also N-terminally extended forms of at least NKA. At least three receptor types are known for the three principal neurokinins. Based upon their relative selectivities favoring the neurokinin agonists SP, NKA and NKB, the receptors are classified as neurokinin 1 ($NK_1$), neurokinin 2 ($NK_2$) and neurokinin 3 ($NK_3$) receptors, respectively.

It is now recognized that anxiety, stress, and depression are interrelated conditions (File S E *Pharmacol, Biochem & Behavior* 54/1:3–12, 1996). Moreover, these complex emotional states cannot be due simply to defects in a single neurotransmitter although 5-HT has been ascribed a principal role (Graeff et al., *Pharmacol, Biochem & Behavior* 54/1: 129–141, 1996). Substance P(SP) was one of the first neuropeptides to be identified in mammalian brain and it is now accepted that all three tachykinins are found within the CNS (Iversen L L *J Psychopharmacol* 3/1: 1–6, 1989), particularly in the striatonigral neurons, hypothalamus and limbic forebrain (ibid). $NK_1$ and $NK_3$ receptors have been identified in the brain as well (Beaujouan et al., *Neurosci.* 18: 857–875, 1986). Controversy has existed regarding the presence of the $NK_2$ receptor in brain, although recent evidence shows receptor localization in at least the septal region (Steinberg et al., *Eur J Neurosci* 10/7:2337–45 1998).

Pharmacological evidence supporting a role for either $NK_1$ or $NK_2$ receptors in anxiety disorders has been accumulating from assorted animal behavioral tests (for examples, see Table 1). Animal models of depression, however, have been used rarely to define the potential utility of NK receptor antagonists. SP stimulates the turnover of other neurotransmitters involved in depression, i.e., 5-HT in the raphe nucleus, an area thought to be linked to depressive phenomena (Forchetti et al., *J. Neurochem.* 38: 1336–1341, 1982). When injected centrally to nuclei responsible for control of emotion and stress, SP evokes a hemodynamic pressor response bridging this peptide to stress induced hypertension (Ku et al., *Peptides;* 19/4:677–82, 1998). Moreover, rises in both heart rate and mean arterial blood pressure evoked by physical stress can be blocked in rodents by centrally administered $NK_1$ receptor antagonists (Culman et al., *J Pharmacol Exp Ther* 280/1:238–46, 1997).

TABLE 1

Neurokinin receptor antagonist activity in behavioral tests of anxiety/depression.

| Author | Cpd (Receptor type) | Behavioral Test | Outcome |
| --- | --- | --- | --- |
| Teixeira et al., Eur J Pharmacol 5;311(1):7–14, 1996. | $NK_1$ agonists & FK888 ($NK_1$) SR48968 ($NK_2$) | Elevated plus-maze | agonists-anxiogenic antagonists-anxiolytic |
| File Pharm Bio B 58(3): 747–752, 1997. | CGP 49823 ($NK_1$) | Social interaction | anxiolytic |
| Vassout et al Neuropeptides 26/S1:38, 1994. | CGP 49823 ($NK_1$) | Social interaction test Elevated plus-maze Forced swim test (depression model) | anxiolytic inactive antidepressant (only at 30 mg/kg bid) |
| Stratton et al., Eur. J. Pharmacol. 250: R11–12, 1993. | GR100679 ($NK_2$) SR48968 ($NK_2$) | Light-dark box | anxiolytic |
| Walsh et al., Psychopharmacology 121:186–191, 1995. | GR159897 ($NK_2$) SR48968 ($NK_2$) | Light-dark box Marmoset human intruder | anxiolytic anxiolytic |

Description

This invention relates to diaminopropyl compounds; methods of using the compounds in the treatment of disease, the use of the compounds in the manufacture of a medicament; and to pharmaceutical compositions containing such compounds. These compounds antagonize the pharmacological actions of the neurokinin 1 ($NK_1$) receptor. These compounds are useful whenever such antagonism is desired. Thus, such compounds are of value in the treatment of those diseases in which Substance P is implicated, for example, in the treatment of major depressive disorder, severe anxiety disorders, stress disorders, major depressive disorder with anxiety, eating disorders, bipolar disorder, substance use disorder, schizophrenic disorders, psychotic disorders, movement disorders, cognitive disorders, depression and/or anxiety, mania or hypomania, aggressive behaviour, obesity, emesis, rheumatoid arthritis, Alzheimer's disease, cancer, oedema, allergic rhinitis, inflammation, pain, gastrointestinal-hypermotility, Huntington's disease, chronic obstructive pulmonary disorder (COPD), hypertension, migraine, bladder hypermotility, or urticaria.

Accordingly, the present invention provides compounds of the general formula

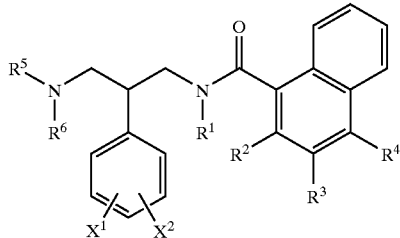

The compounds of the present invention may possess a number of chiral centers, for example at —CH(Ph-$X^1$, $X^2$)—. The present invention covers all isomers, diastereoisomers and mixtures thereof that antagonize $NK_1$.

The preferred configuration at —CH(Ph-$X^1$,$X^2$)— is shown hereinbelow:

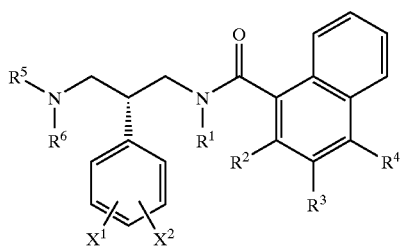

$X^1$ and $X^2$ are independently hydrogen, methyl or halogen. Preferably, $X^1$ and $X^2$ are independently hydrogen or halogen provided that at least one of $X^1$ or $X^2$ is halogen. Most favourably, $X^1$ and $X^2$ are both chloro. In a preferred aspect Ph-$X^1$,$X^2$ is 3,4-dichlorophenyl.

$R^1$ is H or $CH_3$.

$R^2$ is H, halogen, —$OR^7$ or $C_{1-4}$alkyl. In a specific embodiment, $R^2$ is —$OR^7$ or $C_{1-4}$alkyl.

$R^3$ is H, halogen, —$OR^7$ or —CN. In a specific embodiment, $R^3$ is —CN.

$R^4$ is H, halogen, —$OR^7$ or $C_{1-4}$alkyl. In a specific embodiment, $R^4$ is H or $C_{1-4}$alkyl.

$R^5$ is H, $C_{1-8}$alkyl, —C(=O)$R^9$, —C(=O)$OR^8$, —C(=O)N($R^6$)$R^8$, —S(=O)$_n R^9$, cyanoguanidino or $C_{1-4}$acylguanidino.

$R^6$ is, independently at each instance, H or $C_{1-6}$alkyl.

$R^7$ is, independently at each instance, $C_{1-6}$alkyl.

$R^8$ is H, $C_{1-6}$alkyl substituted by 0, 1 or 2 substituents selected from —OH and —NH$R^6$ or $C_{1-3}$alkyl substituted by 1, 2, 3 or 4 halogen atoms.

$R^9$ is, independently at each instance, $C_{1-6}$alkyl substituted by 0, 1 or 2 substituents selected from —OH and —NH$R^6$ or $C_{1-3}$alkyl substituted by 1, 2, 3 or 4 halogen atoms, n is 0, 1 or 2.

Another aspect of the invention involves the use of a compound having the general structure

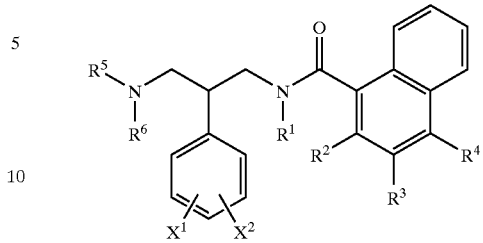

wherein $R^1$–$R^6$ and $X^1$ and $X^2$ are as described above—for the manufacture of a medicament for the treatment of a disease selected from major depressive disorder, severe anxiety disorders, stress disorders, major depressive disorder with anxiety, eating disorders, bipolar disorder, substance use disorder, schizophrenic disorders, psychotic disorders, movement disorders, cognitive disorders, depression and/or anxiety, mania or hypomania, aggressive behaviour, obesity, emesis, rheumatoid arthritis, Alzheimer's disease, cancer, oedema, allergic rhinitis, inflammation, pain, gastrointestinal-hypermotility, Huntington's disease, COPD, hypertension, migraine, bladder hypermotility and urticaria.

Another aspect of the invention involves a pharmaceutical composition comprising a therapeutically-effective amount of an NK1 antagonist having the structure:

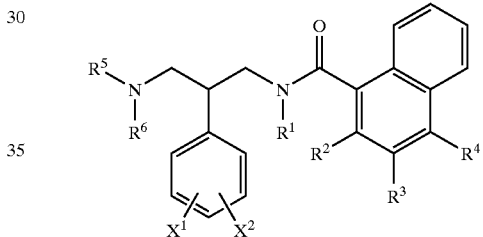

wherein $R^1$–$R^6$ and $X^1$ and $X^2$ are as described above—and a pharmaceutically-acceptable carrier or diluent.

Another aspect of the invention involves a method of treating major depressive disorder, severe anxiety disorders, stress disorders, major depressive disorder with anxiety, eating disorders, bipolar disorder, substance use disorder, schizophrenic disorders, psychotic disorders, movement disorders, cognitive disorders, depression and/or anxiety, mania or hypomania, aggressive behaviour, obesity, emesis, rheumatoid arthritis, Alzheimer's disease, cancer, oedema, allergic rhinitis, inflammation, pain, gastrointestinal-hypermotility, Huntington's disease, COPD, hypertension, migraine, bladder hypermotility, or urticaria comprising administering an effective amount of an $NK_1$ antagonist having the structure:

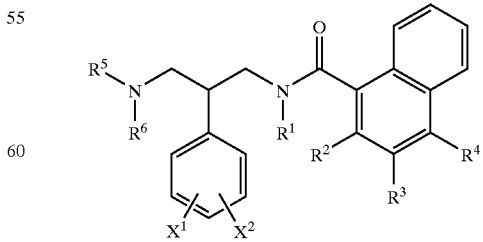

wherein $R^1$–$R^6$ and $X^1$ and $X^2$ are as described above.

Particular compounds of this invention are provided as the Examples hereinbelow.

$C_{Y-Z}$alkyl, unless otherwise specified, means an alkyl chain containing a minimum Y total carbon atoms and a maximum Z total carbon atoms. These alkyl chains may be branched or unbranched, cyclic, acyclic or a combination of cyclic and acyclic. For example, the following substituents would be included in the general description "$C_{4-7}$alkyl":

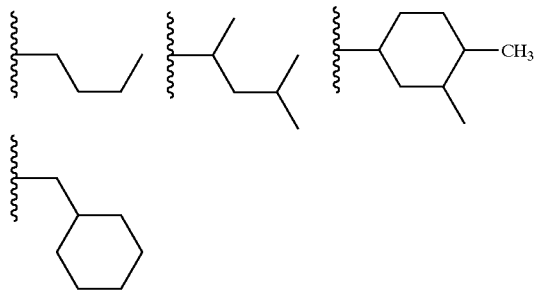

Pharmaceutically-acceptable salts may be prepared from the corresponding acid in conventional manner. Non-pharmaceutically-acceptable salts may be useful as intermediates and as such are another aspect of the present invention.

The term "oxo" means a double bonded oxygen (=O).

Some of the compounds of the present invention are capable of forming salts with various inorganic and organic acids and bases and such salts are also within the scope of this invention. Examples of such acid addition salts include acetate, adipate, ascorbate, benzoate, benzenesulfonate, bisulfate, butyrate, camphorate, camphorsulfonate, citrate, cyclohexyl sulfamate, ethanesulfonate, fumarate, glutamate, glycolate, hemisulfate, 2-hydroxyethyl-sulfonate, heptanoate, hexanoate, hydrochloride, hydrobromide, hydroiodide, hydroxymaleate, lactate, malate, maleate, methanesulfonate, 2-naphthalenesulfonate, nitrate, oxalate, pamoate, persulfate, phenylacetate, phosphate, picrate, pivalate, propionate, quinate, salicylate, stearate, succinate, sulfamate, sulfanilate, sulfate, tartrate, tosylate (p-toluenesulfonate), and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

In order to use a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt and pharmaceutically acceptable carrier.

The pharmaceutical compositions of this invention may be administered in standard manner for the disease condition that it is desired to treat, for example by oral, topical, parenteral, buccal, nasal, vaginal or rectal administration or by inhalation or insufflation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to herein.

The pharmaceutical compositions of this invention will normally be administered to humans so that, for example, a daily dose of 0.01 to 25 mg/kg body weight (and preferably of 0.1 to 5 mg/kg body weight) is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention. For example a tablet or capsule for oral administration may conveniently contain up to 250 mg (and typically 5 to 100 mg) of a compound of the formula (I) or a pharmaceutically acceptable salt thereof. In another example, for administration by inhalation, a compound of the formula (I) or a pharmaceutically acceptable salt thereof may be administered in a daily dosage range of 5 to 100 mg, in a single dose or divided into two to four daily doses. In a flirter example, for administration by intravenous or intramuscular injection or infusion, a sterile solution or suspension containing up to 10% w/w (and typically 0.5% w/w) of a compound of the formula (I) or a pharmaceutically acceptable salt thereof may be used.

Therefore in a further aspect, the present invention provides a compound of the formula (I) or a pharmaceutically acceptable salt thereof for use in a method of therapeutic treatment of the human or animal body.

In yet a further aspect the present invention provides a method of treating a disease condition wherein antagonism of the $NK_1$ receptor is beneficial which comprises administering to a warm-blooded animal an effective amount of a compound of the formula (I) or a pharmaceutically-acceptable salt thereof. The present invention also provides the use of a compound of the formula (I) or a pharmaceutically acceptable salt thereof in the preparation of a medicament for use in a disease condition wherein antagonism of the $NK_1$ receptor is beneficial.

The compounds of the formula (I) and their pharmaceutically acceptable salts may be made by processes as described and exemplified herein and by processes similar thereto and by processes known in the chemical art. If not commercially available, starting materials for these processes may be made by procedures which are selected from the chemical art using techniques which are similar or analogous to the synthesis of known compounds.

It is well known in the art how to prepare optically-active forms (for example, by resolution of the racemic form or by synthesis from optically-active starting materials) and how to determine the $NK_1$ antagonist properties by the standard tests known in the art and those described hereinafter.

Some individual compounds within the scope of this invention may contain double bonds. Representations of double bonds in this invention are meant to include both the E and the Z isomer of the double bond. Additionally, some species within the scope of this invention may contain one or more asymmetric centers. This invention includes the use of any of the optically pure stereoisomers as well as any combination of stereoisomers.

In general, compounds bearing a 2-substituted naphthamide can exist as a mixture of conformational isomers (atropisomers); this is believed to result from slow rotation about the naphthalene amide and/or aryl bonds ("The Chemistry of Rotational Isomers"; Oki, M.; Springer Verlag, NY; 1993). Where individual atropisomers have been isolatable, distinct chemical and biological properties have been observed. The compounds of this invention comprise both mixtures of, and individual, atropisomers.

The following biological test methods, data and Examples serve to illustrate and further describe the invention.

The utility of a compound of the invention or a pharmaceutically acceptable salt thereof (hereinafter, collectively referred to as a "compound") may be demonstrated by standard tests and clinical studies, including those disclosed in the publications described below.

SP Receptor Binding Assay (Test A)

The ability of a compound of the invention to antagonize the binding of SP at the $NK_1$ receptor may be demonstrated using an assay using the human $NK_1$ receptor expressed in Mouse Erythroleukemia (MEL) cells. The human $NK_1$ receptor was isolated and characterized as described in: B. Hopkins, et al. "Isolation and characterization of the human lung $NK_1$ receptor cDNA" *Biochem. Biophys. Res. Comm.* 1991, 180,1110–1117; and the $NK_1$ receptor was expressed in Mouse Erythroleukemia (MEL) cells using a procedure similar to that described in Test B below.

Neurokinin A (NKA) Receptor Binding Assay (Test B)

The ability of a compound of the invention to antagonize the binding of NKA at the $NK_2$ receptor may be demonstrated using an assay using the human $NK_2$ receptor expressed in Mouse Erythroleukemia (MEL) cells, as described in: Aharony, D., et al. "Isolation and Pharmacological Characterization of a Hampster Neurokinin A Receptor cDNA" *Molecular Pharmacology* 1994, 45, 9–19.

The selectivity of a compound for binding at the $NK_1$ and the $NK_2$ receptors may be shown by determining its binding at other receptors using standard assays, for example, one using a tritiated derivative of NKB in a tissue preparation selective for $NK_3$ receptors. In general, the compounds of the invention which were tested demonstrated statistically significant binding activity in Test A and Test B with a $K_i$ of 1 mM or much less typically being measured.

Rabbit Pulmonary Artery: $NK_1$ in Vitro Functional Assay (Test C)

The ability of a compound of the invention to antagonize the action of the agonist Ac—[$Arg^6$, $Sar^9$, $Met(O_2)^{11}$] Substance P (6–11), ASMSP, in a pulmonary tissue may be demonstrated as follows.

Male New Zealand white rabbits are euthanized via i.v. injection into the ear vein with 60 mg/kg Nembutal (50 mg/mL). Preceding the Nembutal into the vein is Heparin (1000 units/mL) at 0.0025 mL/kg for anticoagulant purposes. The chest cavity is opened from the top of the rib cage to the sternum and the heart, lungs and part of the trachea are removed. The pulmonary arteries are isolated from the rest of the tissues and cut in half to serve as pairs.

The segments are suspended between stainless steel stirrups, so as not to remove any of the endothelium, and placed in water-jacketed (37.0° C.) tissue baths containing physiological salt solution of the following composition (mM): NaCl, 118.0; KCl, 4.7; $CaCl_2$, 1.8; $MgCl_2$, 0.54; $NaH_2PO_4$, 1.0; $NaHCO_3$, 25.0; glucose, 11.0; indomethacin, 0.005 (to inhibit cyclooxygenase); and dl-Propranolol, 0.001 (to block $\beta$ receptors); gassed continuously with 95% $O_2$-5% $CO_2$. Responses are measured on a Grass polygraph via Grass FT-03 transducers.

Initial tension placed on each tissue is 2 grams, which is maintained throughout the 1.0 hour equilibration period. Tissues are washed with the physiological salt solution at 15 minute intervals. At the 30 and 45 minute wash the following treatments are added: $1\times10^{-6}$ M Thiorphan (to block E.C.3.4–24.11), $3\times10^{-8}$ M (S)—N—[2-(3,4-dichlorophenyl)-4[4-(2 -oxoperhydropyrimidin-1-yl) piperidino]butyl]-N-methylbenzamide (to block $NK_2$ receptors), and the given concentration of the compound being tested. At the end of the 1.0 h equilibration, $3\times10^{-6}$ M Phenylephrine hydrochloride is added for 1.0 h. At the end of 1.0 h, a dose relaxation curve to ASMSP is done. Each tissue is treated as a individual and is considered finished when it fails to relax further for 2 consecutive doses. When a tissue is complete, $1\times10^{-3}$ M Papaverine is added for maximum relaxation.

Percent inhibition is determined when a tested compound produces a statistically significant (p<0.05) reduction of the total relaxation which is calculated using the total relaxation of the Papaverine as 100%. Potencies of the compounds are determined by calculating the apparent dissociation constants ($K_B$) for each concentration tested using the standard equation:

$$KB=[\text{antagonist}]/(\text{dose ratio}-1)$$

where dose ratio=antilog[(agonist–log molar $EC_{50}$ without compound)–(–log molar $EC_{50}$ with compound)]. The $K_B$ values may be converted to the negative logarithms and expressed as –log molar KB (i.e. $pK_B$). For this evaluation, complete concentration-response curves for agonist obtained in the absence and presence of the compound tested using paired pulmonary artery rings. The potency of the agonist is determined at 50% of its own maximum relaxation in each curve. The $EC_{50}$ values are converted to negative logarithms and expressed as –log molar $EC_{50}$.

$NK_2$ In Vitro Functional Assay (Test D)

The ability of a compound of the invention to antagonize the action of the agonist [$\beta$-ala8] NKA (4–10), BANK, in a pulmonary tissue may be demonstrated as follows. Male New Zealand white rabbits are euthanized via i.v. injection into the ear vein with 60 mg/kg Nembutal (50 mg/mL). Preceding the Nembutal into the vein is Heparin (1000 units/mL) at 0.0025 mL/kg for anticoagulant purposes. The chest cavity is opened from the top of the rib cage to the sternum and a small incision is made into the heart so that the left and right pulmonary arteries can be cannulated with polyethylene tubing (PE260 and PE190 respectively). The pulmonary arteries are isolated from the rest of the tissues, then rubbed over an intimal surface to remove the endothelium, and cut in half to serve as pairs. The segments are suspended between stainless steel stirrups and placed in water-jacketed (37.0° C.) tissue baths containing physiological salt solution of the following composition (mM): NaCl, 118.0; KCl, 4.7; $CaCl_2$, 1.8; $MgCl_2$, 0.54; $NaH_2PO_4$, 1.0; $NaHCO_3$, 25.0; glucose, 11.0; indomethacin, 0.005 (to inhibit cyclooxygenase); gassed continuously with 95% $O_2$-5% $CO_2$. Responses are measured on a Grass polygraph via Grass FT-03 transducers.

Initial tension placed on each tissue is 2 g, which is maintained throughout the 45 min equilibration period. Tissues are washed with the physiological salt solution at 15 min intervals. After the 45 min equilibration period, $3\times10^{-2}$ M KCl is given for 60 min to test the viability of the tissues. The tissues are then washed extensively for 30 min. The concentration of the compound being tested is then added for 30 min. At the end of the 30 min, a cumulative dose response curve to BANK is performed. Each tissue is treated as a individual and is considered finished when it fails to contract further for 2 consecutive doses. When a tissue is complete, $3 \times 10^{-2}$ M $BaCl_2$ is added for maximum contraction.

Percent inhibition is determined when a tested compound produces a statistically significant (p<0.05) reduction of the total contraction which is calculated using the total contraction of the $BaCl_2$ as 100%. Potencies of the compounds are determined by calculating the apparent dissociation constants ($K_B$) for each concentration tested using the standard equation:

$$K_B = [\text{antagonist}]/(\text{dose ratio} - 1)$$

where dose ratio=antilog[(agonist–log molar $EC_{50}$ without compound)–(–log molar $EC_{50}$ with compound)]. The $K_B$ values may be converted to the negative logarithms and expressed as –log molar $K_B$ (i.e. $pK_B$). For this evaluation, complete concentration-response curves for agonist obtained in the absence and presence of the compound tested using paired pulmonary artery rings. The potency of the agonist is determined at 50% of its own maximum relaxation in each curve. The $EC_{50}$ values are converted to negative logarithms and expressed as –log molar $EC_{50}$.

$NK_1$ and $NK_2$ in Vivo Functional Assay (Test E)

The activity of a compound as an antagonist of $NK_1$ and/or $NK_2$ receptors also may be demonstrated in vivo in laboratory animals as described in: Buckner et al. "Differential Blockade by Tachykinin $NK_1$ and $NK_2$ Receptor Antagonists of Bronchoconstriction Induced by Direct-Acting Agonists and the Indirect-Acting Mimetics Capsaicin, Serotonin and 2-Methyl-Serotonin in the Anesthetized Guinea Pig." *J. Pharm. Exp. Ther.*, 1993, Vol 267(3), pp. 1168–1175. The assay is carried out as follows.

Compounds are tested in anesthetized guinea pigs pretreated with i.v. indomethacin (10 mg/kg, 20 min), propranolol (0.5 mg/kg, 15 min), and thiorphan (10 mg/kg, 10 min).

Antagonists or vehicle are administered i.v. and orally, 30 and 120 min prior to increasing concentrations of agonist, respectively. The agonists used in these studies are ASMSP (Ac-[$Arg^6,Sar^9,Met(O_2)^{11}$]-SP(6-11)) and BANK (β-ala-8 NKA4-10).

Administered i.v., ASMSP is selective for $NK_1$ receptors, and BANK is selective for $NK_2$ receptors. Maximum response is defined as zero conductance ($G_L$, 1/Rp). $ED_{50}$ values are calculated (the dose of agonist resulting in a reduction of $G_L$ to 50% of baseline), and converted to the negative logarithm (–log $ED_{50}$). The $ED_{50}$ values, obtained in the presence (P) and absence (A) of antagonist, are used to calculate a Dose Ratio (P/A), an expression of potency. Data are expressed as mean t SEM and statistical differences were determined using ANOVA/Tukey-Kramer and Student's t-test, with p<0.05 considered statistically significant.

Compounds of the present invention exhibit marked activity in the foregoing tests and are considered useful for the treatment of those diseases in which the $NK_1$ and/or $NK_2$ receptor is implicated, for example, in the treatment of asthma and related conditions.

EXAMPLES

The invention will now be illustrated by the following non-limiting examples, in which, unless stated otherwise:

(i) temperatures are given in degrees Celsius (° C.); unless otherwise stated, operations were carried out at room or ambient temperature, that is, at a temperature in the range of 18–25° C.;

(ii) organic solutions were dried over anhydrous magnesium sulfate; evaporation of solvent was carried out using a rotary evaporator under reduced pressure (600–4000 Pascals; 4.5–30 mm Hg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) melting points are uncorrected and (dec) indicates decomposition;

(vi) final products had satisfactory proton nuclear magnetic resonance (NMR) spectra;

(vii) when given, NMR data is in the form of delta values for major diagnostic protons, given in parts per million (ppm) relative to tetramethylsilane (TMS) as an internal standard, determined at 300 MHz using deuterated chloroform ($CDCl_3$) as solvent; conventional abbreviations for signal shape are used; for AB spectra the directly observed shifts are reported; coupling constants (J) are given in Hz; Ar designates an aromatic proton when such an assignment is made;

(viii) reduced pressures are given as absolute pressures in pascals (Pa); elevated pressures are given as gauge pressures in bars;

(ix) solvent ratios are given in volume:volume (v/v) terms; and (x) Mass spectra (MS) were run using an automated system with atmospheric pressure chemical ionization (APCI). Generally, only spectra where parent masses are observed are reported. The lowest mass major ion is reported for molecules where isotope splitting results in multiple mass spectral peaks (for example when chlorine is present).

Terms and abbreviations: solvent mixture compositions are given as volume percentages or volume ratios. In cases where the NMR spectra are complex, only diagnostic signals are reported, atm =atmospheric pressure, Boc=t-butoxycarbonyl, Cbz=benzyloxy-carbonyl, DCM= methylene chloride, DIPEA=diisopropylethylamine, DMF= N,N-dimethylformamide, DMSO=dimethyl sulfoxide, $Et_2O$=diethyl ether, EtOAc=ethyl acetate, equiv.= equivalent(s), h=hour(s), HPLC=high performance liquid chromatography, min=minutes, NMR=nuclear magnetic resonance, psi=pounds per square inch, TFA=trifluoroacetic acid, TBF=tetrahydrofuran.

Standard reductive amination refers to the typical procedure in which a solution of an amine (1–1.2 equiv.), an aldehyde (1–1.2 equiv.) and acetic acid (2 equiv.) is stirred in methanol for 5 to 60 min before adding $NaBH_3CN$ (1.7 equiv.). After 1–16 h the reaction is optionally concentrated, dissolved in DCM, and washed with saturated sodium bicarbonate and then purified by chromatography.

Standard Swern oxidation conditions refer to the oxidation of an alcohol to the corresponding aldehyde according to Mancuso, A J; Huang, S L; Swern, D; J. Org. Chem.; 1978, 2840.

Standard formation of an acid chloride refers to the typical procedure in which a solution of a substituted carboxylic acid in DCM is stirred with 1–1.2 equiv. of oxalyl chloride and a catalytic amount of DMF for 1–12 h, concentrated under reduced pressure, and used without purification.

Standard acylation refers to the typical procedure in which an acid chloride (1–1.2 equiv.) is added to a stirred solution of an amine (1–1.2 equiv.) and triethylamine (2 equiv.) in DCM. After 1–16 h the reaction is optionally concentrated, dissolved in DCM, and washed with saturated sodium bicarbonate and then purified by chromatography.

Where noted that a final compound was converted to the citrate salt, the free base was combined with citric acid (1.0 equiv.) in methanol, concentrated under reduced pressure and dried under vacuum (25–70° C.). When indicated that a compound was isolated by filtration from $Et_2O$, the citrate salt of the compound was stirred in $Et_2O$ for 12–18 h, removed by filtration, washed with $Et_2O$, and dried under vacuum at 25–70° C.

Where noted that a final compound was converted to the hydrochloride salt, a solution of HCl in Et$_2$O was added with stirring to a solution of the purified free base in DCM or methanol. The resulting precipitate was collected by filtration and dried under vacuum.

Some compound bearing a 2-substituted naphthamide existed as a mixture of conformational isomers (atropisomers); this is believed to result from slow rotation about the amide and/or aryl bonds. Such compounds generally showed multiple peaks in HPLC chromatograms and highly complex NMR spectra. In some cases, the individual components of an atropisomeric mixture could be purified by reverse phase HPLC and the properties could be independently evaluated.

Analytical HPLC conditions employed were the following: Hewlett Packard HP1100 system using a Luna C18(2) 4.6×75 mm, 3 micron column (Phenomenex; Torrance, Calif.) with the following gradient: 0–0.5 min; 20% Solvent B, then ramping linearly to 85% Solvent B at 15 min at a fixed flow rate of 2 mL/min (Solvent A: 0.1% TFA in water; Solvent B: 0.1% TFA in methanol) using UV detection at 255 nm.

Mass spectral data; (APCI) m/z. Multiple peaks due to isotopic splitting are not considered; data for the major isotopically abundant signal corresponding to the protonated molecular ion cluster is given (unless noted otherwise).

Example 1

N-[2-(S(3,4-Dichlorophenyl)-3-trifluoroacetylaminopropyl]-N-methyl-3-cyano-2-methoxy-1-naphthamide

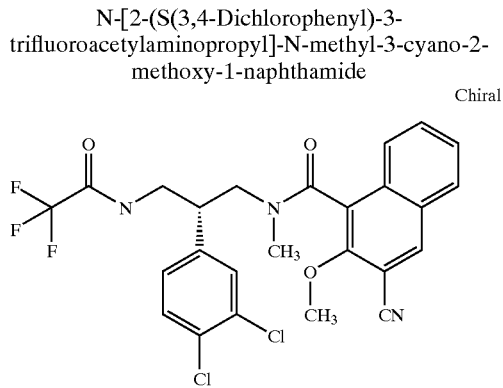

Chiral

N-[2-(S)-(3,4-Dichlorophenyl)-3-carboxypropyl]-N-methyl-3-cyano-2-methoxy-1-naphthamide (0.278 g, 0.58 mmol) was converted to the corresponding acid chloride using oxalyl chloride using the standard defined conditions. Based on the method in Pfister, J. R, and Wyman, W. E., *Synthesis*, 1983, 38, the acid chloride, NaN$_3$ (0.049 g, 0.76 mmol) and (Bu)$_4$NBr (30 mg) was stirred vigorously in a mixture of water (2 mL) and DCM (4 mL) at 0° C. for 2 h. The organic layer was dried and was combined with TFA (0.068 mL, 0.88 mmol) and heated under reflux overnight. The solution was washed with saturated NaHCO$_3$, dried, concentrated, and purified by chromatography (0–10% MeOH in DCM) to afford the product as a white foam (0.206 g). $^1$H NMR (300 MHz, DMSO-d$_6$) d 9.51 (m), 9.32 (m), 8.69–8.63 (m), 8.07–6.41 (m), 4.48–4.43 (m), 4.05–2.27 (m); MS APCI, m/z=538 (M$^+$); HPLC 12.50, 12.78, 13.49.

The requisite N-[2-(S)-(3,4-dichlorophenyl)-3-carboxypropyl]-N-methyl-3-cyano-2-methoxy-1-naphthamide was prepared as follows.

(a) 3-Hydroxy-4-iodo-2-naphthoic acid

A mixture of NaOH (2.12 g) in methanol (100 mL) was stirred until the solution was homogeneous. Sodium iodide (3.98 g) and 3-hydroxy-2-naphthoic acid (5.00 g) were added and allowed to stir for 30 min. The resulting suspension was cooled to 0° C. and a 5.25% (w/v) aqueous solution of sodium hypochlorite was added dropwise and stirring continued for 1 h. Saturated sodium thiosulfate (25 mL) was added and after 5 min the solution was acidified to pH 2 by addition of 6 N HCl resulting in the formation of a yellow precipitate which was filtered and washed with water (50 mL). The precipitate was transferred to a round-bottomed flask, dissolved in methanol (70 mL) and toluene (100 mL), concentrated, redissolved in methanol (70 mL), concentrated, redissolved again in methanol (70 mL) and toluene (100 mL) and concentrated to afford the product as a yellow solid (6.26 g). MS m/z 313 (M−1). $^1$H NMR (DMSO-d$_6$): δ 12.41 (broad, 1 H), 8.63 (s, 1 H), 8.05–7.97 (m, 2 H), 7.70 (m, 1 H), 7.42 (m, 1H).

(b) Methyl 3-methoxy-4-iodo-2-naphthoate

A solution of 3-hydroxy-4-iodo-2-naphthoic acid (8.0 g), dimethyl sulfate (8.03 g), powdered potassium carbonate (8.80 g), and dry acetone (150 mL) was heated under reflux for 18 h. The solution was cooled to room temperature, triethylamine (15 mL) was added, and stirring continued for 30 min. The solution was filtered through a pad of Celite and washed with dry acetone (50 mL). The filtrate was concentrated to a yellow oil, diluted with EtOAc, and washed successively with 1N HCl (100 mL), saturated aqueous sodium bicarbonate (100 mL), and brine (100 mL). The organic phase was dried (sodium sulfate), filtered, concentrated, and purified by chromatography (0–10% EtOAc in hexanes) to afford the product as a yellow oil (5.53 g). $^1$H NMR (DMSO-d$_6$) d 8.47 (s, 1 H), 8.09 (m, 2 H), 7.74 (m, 1 H), 7.61 (m, 1 H), 3.94 (s, 3 H), 3.87 (s, 3 H).

(c) 1-Iodo-3-cyano-2-methoxynaphthalene

Based on the procedure of Wood, J L; Khatri, N A; Weinreb, S M; Tetrahedron Lett; 51, 4907 (1979), methyl 3-methoxy-4-iodo-2-naphthoate (5.0 g) was suspended in xylenes (100 mL), cooled to 0° C., dimethylaluminum amide solution (approximately 37 mmol) was added and the solution heated under reflux for 2.5 h. The solution was then cooled to 0° C. and the solution was acidified to pH 2 by addition of 1N HCl and extracted with EtOAc (3×100 mL). The combined EtOAc extracts were washed with saturated aqueous sodium bicarbonate (150 mL) and brine (150 mL), dried (sodium sulfate), filtered, concentrated, and purified by chromatography (1:1 EtOAc:DCM, then 10–20% EtOAc in DCM) to afford the product as a white solid (3.29 g). $^1$H NMR (DMSO-d$_6$): δ 8.69 (s, 1 H), 8.24–8.04 (m, 2 H), 7.91–7.81 (m, 1 H), 7.76–7.65 (m, 1 H), 3.99 (s, 3 H); MS m/z 311 (M+H).

(d) Methyl 3-cyano-2-methoxy-1-naphthoate

Through a suspension of 1-iodo-3-cyano-2-methoxynaphthalene (0.250 g), Pd(OAc)$_2$ (0.018 g), triethylamine (0.081 g) and methanol (20 mL) was bubbled carbon monoxide for 25 min, then stirred at 70° C. under carbon monoxide (1 atm) for 18 h. The cooled solution was filtered, rinsed with methanol (20 mL) and DCM (20 mL), concentrated, preadsorbed onto silica (1 g) and purified by chromatography (0–10% EtOAc in hexanes) to afford the product as a white solid (0.113 g). $^1$H NMR (DMSO-d$_6$): δ 8.78 (s, 1 H), 8.12–8.09 (m, 1 H), 7.84–7.78 (m, 2 H), 7.70–7.63 (m, 1 H), 4.02–4.01 (m, 6 H); IR (cm$^{-1}$): 2228, 1724, 1296, 1236, 1208, 1017.

(e) 3-Cyano-2-methoxy-1-naphthoic acid

A solution of methyl 3-cyano-2-methoxy-1-naphthoate (0.113 g) and LiOH·H$_2$O (0.0196 g) THF (3 mL), water (1 mL) and methanol (1 mL) was stirred overnight at room temperature. The solution was diluted with saturated sodium bicarbonate and extracted with Et$_2$O. The aqueous layer was acidified to pH 2 by addition of 1N HCl and extracted with Et$_2$O. The organic layer was washed with water (30 mL) and brine (40 mL), dried (sodium sulfate), filtered, and concentrated to a white solid. $^1$H NMR (DMSO-d$_6$): δ 14.06 (broad, 1 H), 8.08–8.02 (m, 1 H), 7.83–7.76 (m, 2H), 7.69–7.63 (m, 1 H), 4.02 (s, 3 H); MS m/z: 226 (M−1).

(f) N-[2S)-(3,4-Dichlorophenyl)-4-hydroxybutyl]-N-methyl-3-cyano-2-methoxy-1-naphthamide A solution of N-[2-(S)-(3,4-dichlorophenyl)₄-hydroxybutyl]-N-methylamine (Miller, SC; WO 9512577) in DCM was combined with 10% aqueous sodium bicarbonate solution. The mixture was cooled to 0° C. and a solution of 3-cyano-2-methoxy-1-naphthoyl chloride in DCM was added dropwise over 30 min. After stirring overnight at room temperature, the organic phase was concentrated and purified by column chromatography to afford N-[2-(S)-(3,4-dichlorophenyl)-4-hydroxybutyl]-N-methyl-3-cyano-2-methoxy-1-naphthamide. ¹H NMR (300 MHz, DMSO-d₆) d 8.67–8.58 (m), 8.07–8.00 (m), 7.72–7.65 (m), 7.64–7.43 (m 7.42–7.34 (m), 7.02–7.01 (m), 6.98–6.87 (d), 6.77–6.74 (d), 6.31–6.28 (d), 4.55–4.52 (t), 4.35–4.34 (t), 4.03–3.92 (m), 3.78–3.72 (m), 3.68 (s), 3.45–3.37 (m), 3.29–2.89 (m), 2.73 (s), 2.59–2.49 (m), 1.91–1.78 (m), 1.58–1.46 (m); MS APCI, m/z=457 (M+).

(g) N-[2-(S)-(3,4-Dichlorophenyl)-3-carboxypropyl]-N-methyl-3-cyano-2-methoxy-1-naphthamide

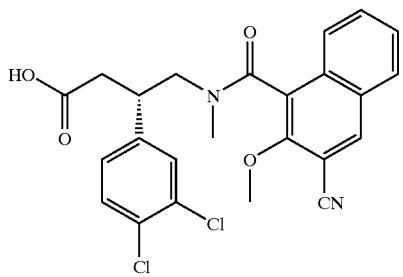

According to the procedure of Corey, E J and Schmidt, G, Tetr. Lett., 1979, 399, a solution of pyridinium dichromate (4.5 g) was added to a solution of N-[2-(S)-(3,4-dichlorophenyl)-4-hydroxybutyl]-N-methyl-3-cyano-2-methoxy-1-naphthamine(1.5 g) in DMF (20 mL) and stirred for 4 h. After filtration, dilution with ethyl acetate, and aqueous extraction of the filtrate, the product was purified by flash chromatography (80%). ¹H NMR (300 MHz, DMSO-d₆) d 12.28 (s), 8.66–8.62 (m), 8.09–7.95 (m), 7.78–7.76 (m), 7.72–7.56 (m), 7.52–7.45 (m), 7.40–7.30 (m), 7.11–7.10 (d), 7.04 (s), 7.01 (s), 6.87–6.84 (d), 4.53–4.45 (t), 3.94 (s), 3.92 (s), 3.68 (s), 3.44–3.27 (m), 3.11 (s), 3.02 (s), 2.76–2.73 (m), 2.62 (s), 2.55–2.38 (m); MS APCI, m/z=471 (M⁺).

Example 2

N-[2-(S)-(3,4-Dichlorophenyl)₃-aminopropyl]-N-methyl-3-cyano-2-methoxy-1-naphthamide

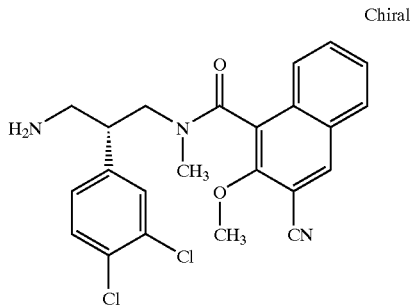

A solution of the material Example 1 (1.00 g, 1.85 mmol) and 1N NaOH (3.7 mL, 3.7 mmol) was stirred in MeOH (5 mL) for 2 h, then extracted into EtOAc. The organic layer was dried, concentrated and purified by chromatography (0–10% MeOH in DCM) to afford the product as a pale yellow foam (0.569 g) and converted to the citrate salt. ¹H NMR (300 MHz, DMSO-d₆) d 8.70–8.63 (m), 8.09–6.80 (m), 6.54–6.51 (d, J=8.4 Hz), 4.39–4.31(m), 4.07–2.27 (m); MS APCL, m/z=442 (M⁺); HPLC 8.77, 9.24, 10.24, 10.38.

Example 3

N-[2S (3,4-Dichlorophenyl)-3-N',N'-dimethylaminopropyl]-N-methyl-3-cyano-2-methoxy-1-naphthamide

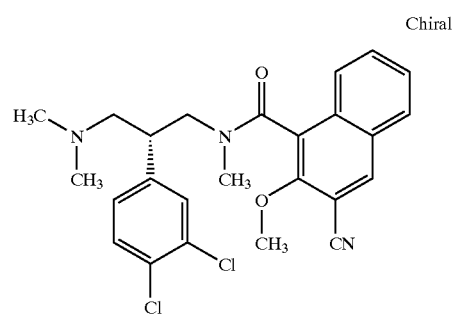

A solution of the material of Example 2 (0.100 g, 0.22 mmol), 37% formaldehyde in H₂O (2 mL), and 99% formic acid (0.069 mL, 1.80 mmol) was heated under reflux for 18 h. To the cooled mixture was added 1M HCl (1 mL) and 1M NaOH to adjust to pH 11, then extracted with EtOAc, washed with brine, dried, concentrated and purified by chromatography (0–6% MeOH in DCM-containing 0.1% concentrated NH₄OH) to afford the product as a white foam (97 mg) which was converted to the citrate salt. ¹H NMR (300 MHz, DMSO-d₆) d 8.69–8.63 (m), 8.12–6.86 (m), 6.33–6.30 (d, J=8.4 Hz), 4.50–4.42 (m), 4.05–1.96 (m); MS APCI, m/z=470 (M⁺); HPLC 8.63, 9.00, 10.05, 10.28.

Example 4

N-[2-(S)-(3,4-Dichlorophenyl]3-(N'-cyanoguanidino)propyl)]-N-methyl-3-cyano-2-methoxy-1-naphthamide

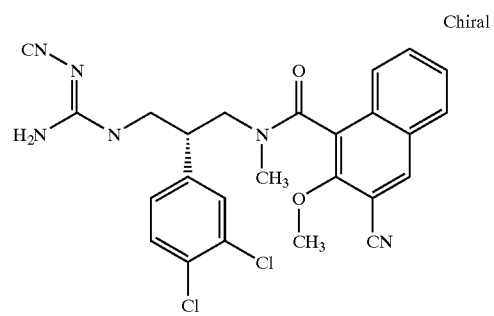

A solution of 1 N HCl (0.339 mL, 0.339 mmol), 1-butanol (0.70 mL), and NaN(CN)₂ (0.034 g, 0.389 mmol) was stirred for 5 min followed by addition of the material of Example 2 (0.150 g, 0.339 mmol). The solution was heated under reflux for 2 h, stirred at room temperature overnight, concentrated, and purified by chromatography (0–4% MeOH in DCM) to afford the product as a yellow solid (0.088 g). ¹H NMR (300 MHz, DMSO-d₆) d 8.65–8.61 (m), 8.08–6.46 (m), 4.44–2.27 (m); MS (MALDI-TOF), m/z=509 (M⁺); HPLC 11.33, 11.45, 12.15, 12.26.

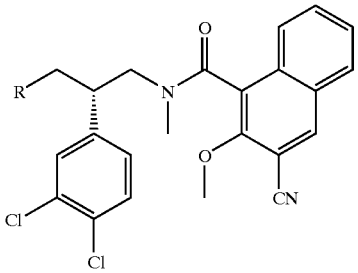

| Ex. | R | MS[a] | HPLC[b] | Salt form[c] | Synthesis |
|---|---|---|---|---|---|
| 5 | —NHC(=O)—OCH₂CH₃ | 514 | 12.51, 12.81, 13.39 | C | Ethyl chloroformate[d] |
| 6 | —NHS(=O)₂CH₃ | 520 | 10.98, 11.38, 12.16 | C | Methanesulfonyl chloride[d] |
| 7 | —NHC(O)N—(CH₃)₂ | 513 | 11.42, 11.78, 12.68 | C | Dimethyl-carbamyl chloride[d] |
| 8 | —N(CH₃)C(O)CF₃ | 552 | 13.12, 13.35, 13.92 | C | Methyl iodide[e] |
| 9 | —NHCH₃ | 456 | 8.73, 9.18, 10.18, 10.32 | A | Sodium hydroxide[f] |

[a] Mass spectral data; (APCI) m/z. Multiple peaks due to isotopic splitting are not considered; data for the major isotopically abundant signal corresponding to the protonated molecular ion cluster are shown (unless noted otherwise).
[b] See general experimental section for HPLC conditions, retention times in minutes; "nd" indicates not determined.
[c] Salt forms: A, citrate; B, iodide; C; not applicable, D, fumarate; E, trifluoroacetate.
[d] The indicated acylating agent (acid chloride, chloroformate or sulfonyl chloride) was reacted with the material of Example 2 using the standard defined conditions for acylation. In cases where the acylating agent was a chloroformate or sulfonyl chloride, these reagents were used in place of the acid chloride in the general procedure.
[e] Using typical conditions, a solution of the material of Example 1 was stirred overnight with NaH (1 equiv.) and methyl iodide (2 equiv.) in DMF, recovered by extraction, and purified by chromatography (50–100% DCM in hexane).
[f] The material of Example 8 was reacted with methanolic NaOH according to the method described for Example 2.

Example 10

N-[2-(S)-(3,4-dichlorophenyl)-3-aminopropyl]-3-cyano-2-ethyl-1-naphthamide Citrate (1:1)

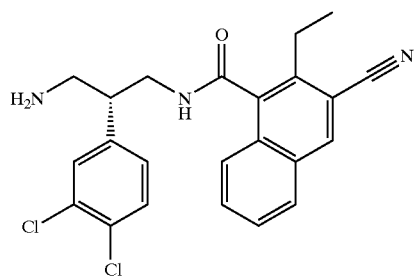

(a) To a stirred solution of N-[2-(S)-(3,4-dichlorophenyl)-3-carboxypropyl]-3-cyano-2-ethyl-1-naphthamide (0.51 mmol) and triethylamine (1.1 equiv.) in acetonitrile (10 mL) was added diphenylphosphorylazide (1.4 equiv.). After 3 h at room temperature, the solution was heated (20 min @65° C.), allowed to re-cool, and 10% aqueous HCl (1 mL) was added. After stirring overnight, the mixture was concentrated, treated with saturated aqueous sodium bicarbonate, and extracted with EtOAc. The EtOAc extracts were concentrated, and the residue was purified by flash chromatography. The purified free base (22%) was converted to the citrate salt and isolated by filtration from Et₂O. MS APCl, m/z=426 (M⁺) (free base); HPLC [a] 15.0.

[a] Analytical HPLC conditions employed were the following: Hewlett Packard HP 1050 system using a Zorbax RX-C8, 4.6×250 mm, 5 micron column at 30° C., with the following gradient: 0–0.5 min; 10% Solvent B, then ramping linearly to 100% Solvent B at 30 min at a fixed flow rate of 1.2 mL/min (Solvent A: 0.1% TFA in water; Solvent B: 0.1% TFA in acetonitrile); UV detection at 215 and 260 nm; retention time given in min.

(b) N-[2-(S)-(3,4-dichlorophenyl)-3-carboxypropyl]-3-cyano-2-ethyl-1-naphthamide

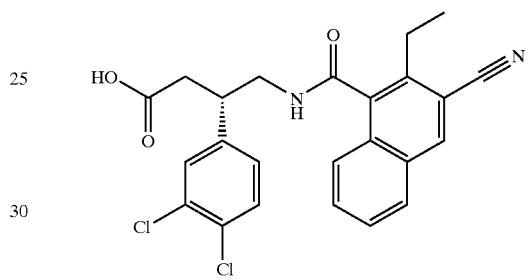

A solution containing N-[2-(S)-(3,4-Dichlorophenyl)-4hydroxybutyl]-3-cyano-2ethyl-1-naphthamide (2.5 mmol) in acetone (10 mL) was added over several minutes to a cooled (ice bath) solution containing Jones Reagent (2 mL) [See "Reagents for Organic Synthesis" (Fieser & Fieser), Vol. 1, Pg 142 and references therein.] in acetone (20 mL). After 2.5 h, the brownish mixture was treated with isopropanol (4 mL), stirred 15 min, then treated with water and extracted with EtOAc. The EtOAc extracts were concentrated to give the required product (theory) as a tan form. MS APCI, m/z=455 (M⁺).

(c) N-[2-(S)-(3,4-Dichlorophenyl)-4-hydroxybutyl]-3-cyano-2-ethyl-1-naphthamide

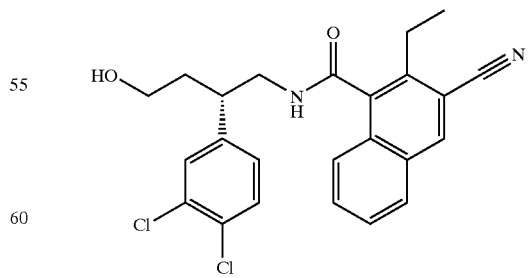

Prepared from the amino-alcohol by acylation with the acid chloride as in Example 1(f).

What is claimed is:

1. A compound having the formula

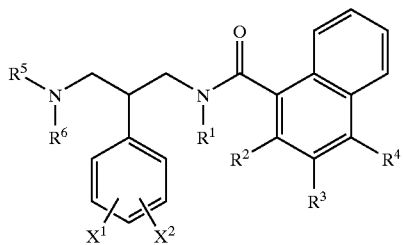

wherein:
R$^1$ is H or CH$_3$;
R$^2$ is H, halogen, —OR$^7$ or C$_{1-4}$alkyl;
R$^3$ is H, halogen, —OR$^7$ or —CN;
R$^4$ is H, halogen, —OR$^7$ or C$_{1-4}$alkyl;
R$^5$ is H, C$_{1-8}$alkyl, —C(=O)R$^9$, —C(=O)OR$^8$, —C(=O)N(R$^6$)R$^8$, —S(=O)$_n$R$^9$, cyanoguanidino or C$_{1-4}$acylguanidino;
R$^6$ is independently at each instance, H or C$_{1-6}$alkyl;
R$^7$ is, independently at each instance, C$_{1-6}$alkyl;
R$^8$ is H, C$_{1-6}$alkyl substituted by 0, 1 or 2 substituents selected from —OH and -NHR$^6$ or C$_{1-3}$alkyl substituted by 1, 2, 3 or 4 halogen atoms;
R$^9$ is, independently at each instance, C$_{1-6}$alkyl substituted by 0, 1 or 2 substituents selected from —OH and —NHR$^6$ or C$_{1-3}$alkyl substituted by 1, 2, 3 or 4 halogen atoms;
n is 0, 1 or 2; and
X$^1$ and X$^2$ are independently H, —CH$_3$ or halogen; or any pharmaceutically-acceptable salt thereof.

2. A compound according to claim 1, wherein X$^1$ and X$^2$ are H or halogen, and at least one of X$^1$ and X$^2$ are halogen.

3. A compound according to claims 1, wherein R$^2$ is —OR$^7$ or C$_{1-4}$alkyl.

4. A compound according to claim 1, wherein R$^3$ is —CN.

5. A compound according to claim 1, wherein R$^4$ is H or C$_{1-4}$alkyl.

6. A pharmaceutical composition comprising:
a therapeutically-effective amount of an NK$_1$ antagonist according to claim 1; and
a pharmaceutically-acceptable carrier or diluent.

* * * * *